United States Patent [19]

Stearns

[11] 4,281,679
[45] * Aug. 4, 1981

[54] FLOW CONTROL MEANS FOR USE IN AN ADAPTOR ASSEMBLY

[76] Inventor: Stanley D. Stearns, P.O. Box 55603, Houston, Tex. 77055

[*] Notice: The portion of the term of this patent subsequent to Nov. 6, 1996, has been disclaimed.

[21] Appl. No.: 69,789

[22] Filed: Aug. 27, 1979

[51] Int. Cl.³ .............................................. F16K 15/04
[52] U.S. Cl. ................................. 137/515.5; 137/550; 137/533.11; 285/342; 285/353
[58] Field of Search ................. 285/177, 18, 342, 343, 285/353, 354; 137/515.5, 550, 533.11

[56] References Cited

U.S. PATENT DOCUMENTS

| | | | |
|---|---|---|---|
| 1,652,765 | 12/1927 | Cowles | 285/177 |
| 1,665,346 | 4/1928 | Clarke | 285/177 |
| 1,726,804 | 9/1929 | Byers | 137/515.5 |
| 1,764,186 | 6/1930 | Teesdale | 137/515.5 |
| 1,797,277 | 3/1931 | Thomas | 285/342 |
| 1,883,273 | 10/1932 | Zerk | 285/343 |
| 1,993,732 | 3/1935 | Bijur | 285/177 |
| 3,367,362 | 2/1968 | Hoffman | 137/515.5 |
| 4,173,363 | 11/1979 | Stearns | 285/177 |

FOREIGN PATENT DOCUMENTS

| | | | |
|---|---|---|---|
| 1048103 | 12/1958 | Fed. Rep. of Germany | 285/177 |
| 955798 | 1/1950 | France | 137/515.5 |
| 1024948 | 4/1953 | France | 137/515.5 |

*Primary Examiner*—Martin P. Schwadron
*Assistant Examiner*—H. Jay Spiegel
*Attorney, Agent, or Firm*—Gunn, Lee & Jackson

[57] ABSTRACT

An adaptor assembly for connecting a tubing with either a male or female fitting is disclosed. Flow control means within the adaptor assembly comprise an important feature of the disclosed and preferred embodiment wherein the flow control means comprises a filter. The filter is a disk of filtrant material such as a nonwoven fiber formed into a pad of specified thickness and cut in a circle. It is placed adjacent to a shoulder in the adaptor and is supported by a surrounding ring.

An alternate embodiment which is one of the preferred embodiments hereof includes a check valve serving as the flow control means. The check valve is constructed with a circular valve seat having a chamfered shoulder, a spherical valve element which closes against the seat to block flow, a surrounding sleeve which permits the check valve element to move toward and away from the chamfered seat and a transversely extending disk to block the passage. The disk blocks the valve element from escape. The disk is perforated with a number of holes which, in the aggregate, provide a suitable cross-sectional flow area through the adaptor.

5 Claims, 6 Drawing Figures

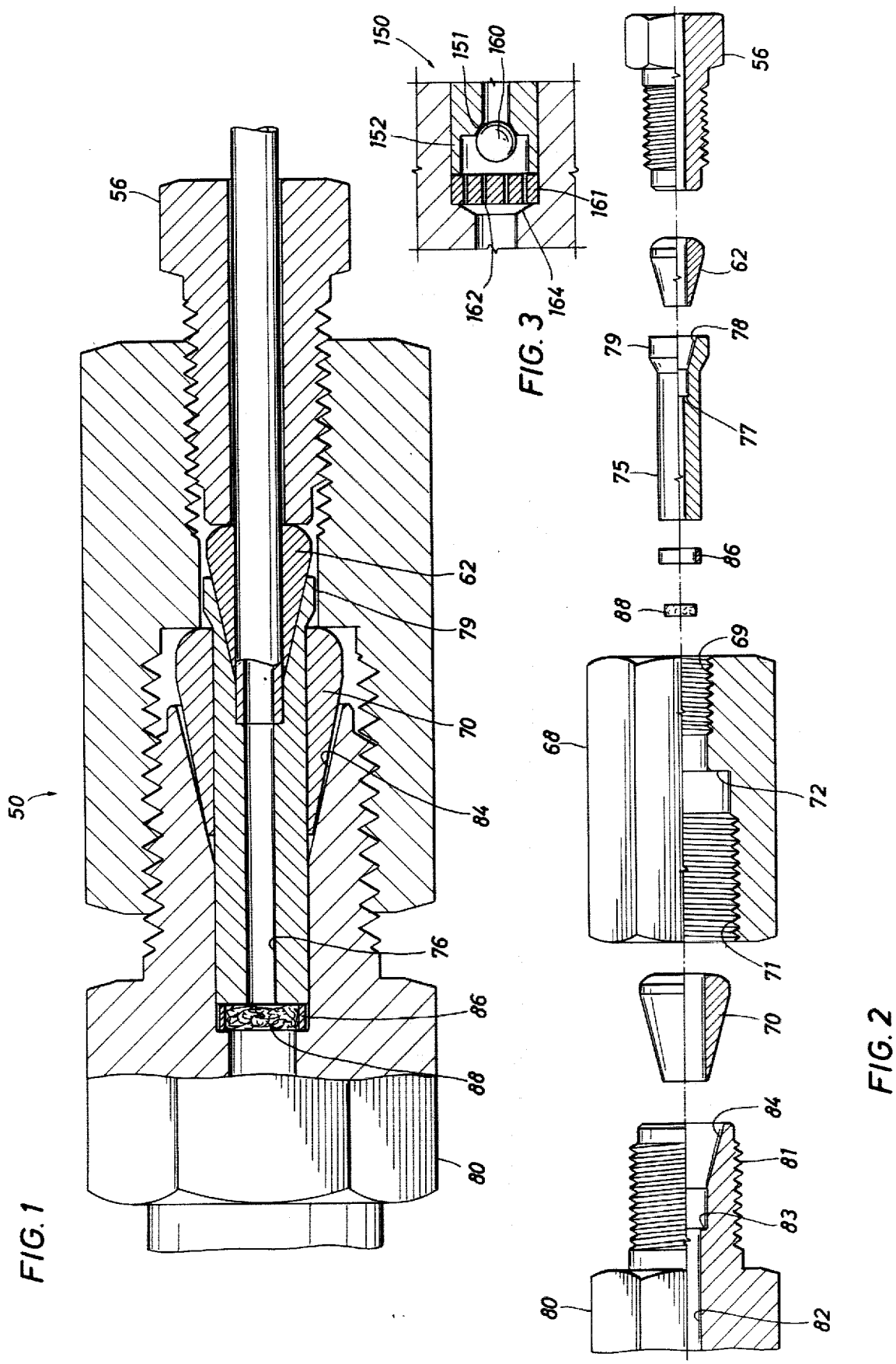

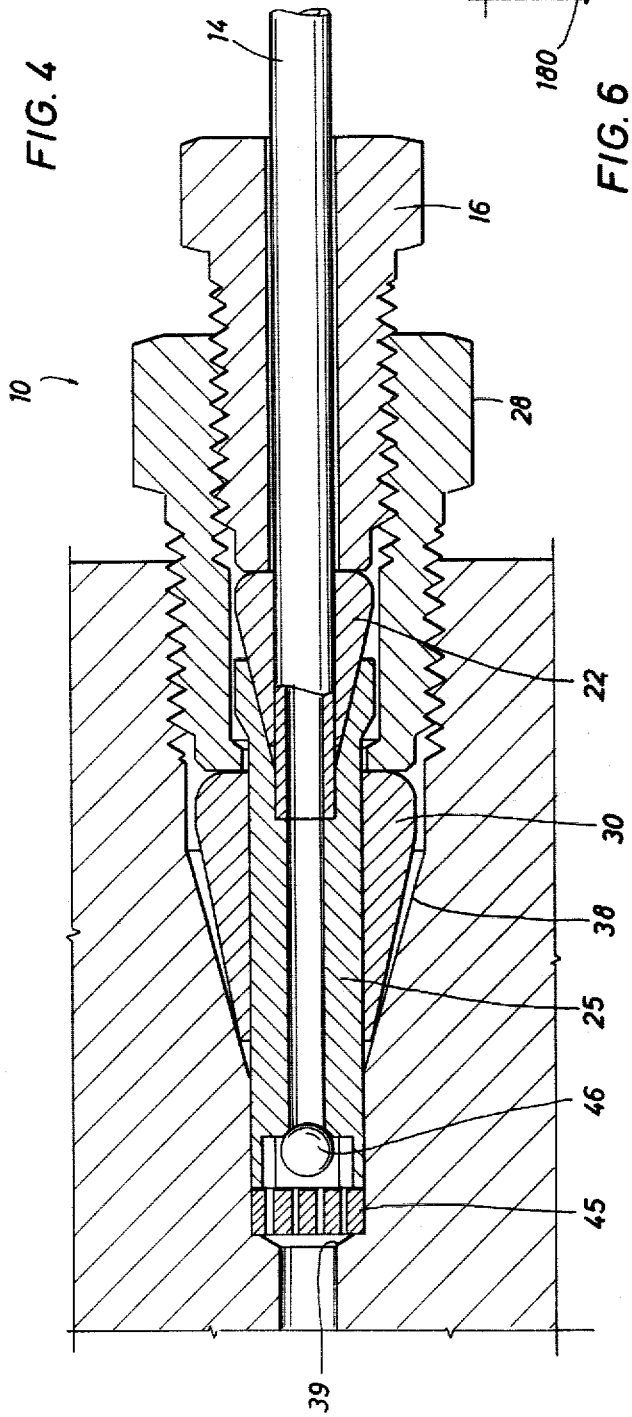
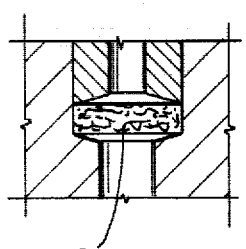
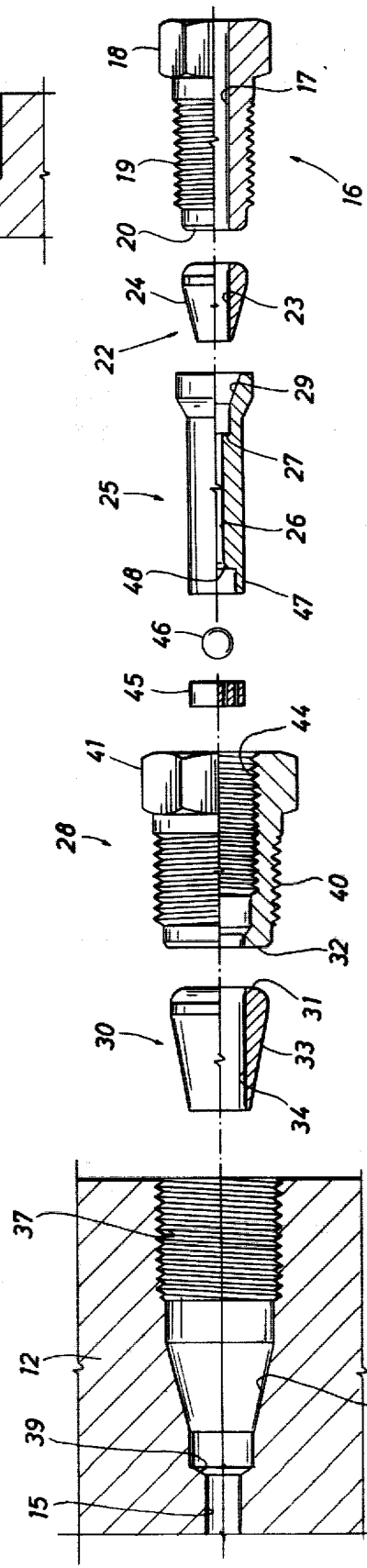

FLOW CONTROL MEANS FOR USE IN AN ADAPTOR ASSEMBLY

BACKGROUND OF THE DISCLOSURE

This apparatus is related to previously filed U.S. application Ser. No. 921,167, filed on July 3, 1978, and which subsequently issued as U.S. Pat. No. 4,173,363. That disclosure is directed to an adaptor assembly for use with a male or female fitting to accommodate mismatches in fitting size and tubing size. This typically arises in the context of laboratory instruments. As an example, a laboratory instrument might have a miniscule flow through a very small tubing. It might be furnished through a somewhat larger tubing. Tubing sizes are typically in the range of about 0.5 inch and smaller. It is quite often necessary to make transitional connections from one size to another to deliver the flow.

The apparatus of this disclosure enhances the previous disclosure in that it provides flow control means which are filters and check valves. The apparatus further includes a filter and check valve construction for installation within an adaptor assembly which enables the filter and check valve to be installed without having its own separate fittings. So to speak, the filter or check valve is installed free of fittings in that the adaptor assembly is used, and, thus, installation is expedited.

BRIEF SUMMARY OF THE APPARATUS

In the male and female versions of the present apparatus, they are constructed and arranged to include means for holding a tubing by clamping action. The entire assembly thus utilizes a hollow, threaded nut which slides loosely around the tubing to be connected and which nut is positioned adjacent to a tapered spool. The nut and spool abut an elongate, hollow sleeve received into a coupling which is threaded at two locations, and, for the female fitting, the coupling is internally and externally threaded. For a male fitting, the coupling is axially threaded with two different sets of threads located at opposite ends and which are adapted to have the same or differing diameters. The coupling jams a second tapered spool into or against the fitting. The end of the tube is externally gripped with a force applied by the tapered member which surrounds it and holds it. The two tapered spools abut corresponding tapered surfaces which initiates a wedging action when the members are screwed together and thereby hold. The elongate, hollow sleeve is utilized to clamp in position either a filter disk formed of nonwoven, fibrous filter material or to secure in location the check valve assembly. The check valve assembly utilizes an end located valve seat on the elongate, tubular sleeve positioned adjacent to a perforated disk. The perforated disk has a number of openings in it to provide flow. The perforated disk is held remote from the valve seat by an upstanding shoulder at the tip of the elongate, hollow sleeve. This defines a cavity to receive a check valve ball which functions as the valve element.

Both male and female adaptor assemblies are disclosed, and each is adapted to receive and support a filter or check valve as required.

BRIEF DESCRIPTION OF THE DRAWINGS

FIG. 1 is a sectional view of an adaptor assembly for a male fitting to connect to a tubing which incorporates a filter within the adaptor assembly;

FIG. 2 is a view of the components shown in FIG. 1 which are in exploded position with the components partly shown in sectional view;

FIG. 3 is a partial view of the structure shown in FIG. 1 which depicts an alternate embodiment having a check valve assembly as opposed to a filter assembly therein;

FIG. 4 is a sectional view of an adaptor assembly connected with a female fitting for clamping and aligning a tube in axial communication with a mismatched opening and further depicting a check valve structure within the adaptor assembly;

FIG. 5 discloses the structure of FIG. 4 in exploded view with the components partly in section to illustrate details of construction; and FIG. 6 shows an alternate embodiment of the adaptor assembly of FIG. 4 including a filter within the adaptor assembly.

DETAILED DESCRIPTION OF THE ILLUSTRATED EMBODIMENTS

Attention is first directed to FIG. 1 of the drawings. FIG. 1 shows the components threaded together and is to be contrasted with the exploded view of FIG. 2. The embodiment shown in FIG. 1 is identified generally by the numeral 50. The same reference numerals found in the referenced earlier disclosure will be applied to the embodiment 50. It thus incorporates a hollow, threaded nut 56, the nut 56 being axially hollow and equipped with a head having suitable wrench flats on it. It includes a neck adjacent to the head and threads of a suitable diameter and pitch along the hollow nut. The nut has an end face opposite the head which abuts a tapered spool 62. The tapered spool 62 is sized to fit around the tubing to be connected to the fitting. The tapered spool 62 has a bulbous end portion abutting the hollow, threaded nut. The exterior is tapered to a narrow or thin wall construction at the opposite end. It is axially hollow to fit around the tubing. The tapered spool is received within an elongate sleeve 75 having an axial passage at 76 which is smaller than the tubing inserted into the assembly. The passage 76 extends along the length of the elongate, hollow sleeve 75 to a shoulder 77. The shoulder 77 is on the interior and serves as a seat to receive the tubing inserted into the apparatus. The shoulder thus terminates an axial, countersunk portion which has a larger diameter. That portion, in turn, is flared at 78 with a counterbore in the form of a taper. A tapered surface thus confronts the tapered spool 62 to enable the two components to nest together. They are telescoped together as shown in FIG. 1. The exterior of the sleeve 75 is cylindrical at the left-hand portions. It is slightly flared at 79. This defines an external enlargement. This prevents the sleeve from achieving a loose relationship with an additional tapered spool 70. The tapered spool 70 is larger than the tapered spool 62, but it is otherwise constructed in approximately the same shape, differing only by changes in proportion. The tapered spool 70 fits on the exterior of the elongate, hollow sleeve 75. The elongate, hollow sleeve 75 has a body length which enables it to more than extend through the tapered spool 70. The external enlargement limits penetration. It extends fully through the axial central passage.

A coupling 68 is included which is axially hollow. It has a first set of threads at 69 located at the right-hand end to enable the threaded nut to be threaded to it. The threaded nut 56 is thus joined to the threads at 69. The threads extend sufficiently along the axial passage. The passage is axially through the coupling. The threads terminate at an adequate depth, and, thereafter, the interior axial passage becomes larger in diameter at a shoulder 72 which faces downstream. The shoulder 72 is immediately adjacent to a second set of threads 71 which mate with a male coupling to be described. The threads 71 define an enlarged, axial internal passage sufficiently large to receive the tapered spool 70. They are sufficiently large to receive the connected fitting. It will be observed that the coupling 68 is equipped with two sets of threads, the two sets being located on the interior.

A male fitting is shown at the left-hand extremity of FIGS. 1 and 2. It includes a head 80 having wrench flats on the surrounding body. This enables a wrench to be placed on it. The male fitting might be formed as an independent coupling or might be integrally constructed with the cabinet, housing or body of a test instrument. The head 80 is immediately adjacent to a set of threads at 81. The threads mesh with the threads 71 on the coupling 68. This enables the two parts to be pulled together. The fitting is axially hollow with a passage at 82. The passage 82 extends to an enlarged passage defined by a shoulder 83. The larger passage emerges in a tapered end opening at 84. The tapered surface 84 receives the tapered spool 70. The surface 84 is tapered at an angle slightly more severe than the angle on the tapered spool 70. As shown in FIG. 1, these two surfaces come close to nesting, but they do not precisely match up. This enables the tapered spool 70 to be driven into the male fitting. Proceeding further with FIG. 2, a spacer 86 is included which fits around a nonwoven, fibrous filter component 88.

Assembly of the components into the configuration of FIG. 1 should be considered. The tubing is first hand held, and the hollow nut 56 is threaded onto it. The tapered spool 62 is next placed on the tubing, and the tubing is jammed into the hollow, elongate sleeve 75. The male fitting is pushed into the coupling 68, capturing the tapered spool 70 therebetween, and they can be partially threaded. Before threading, it is preferable to place the spacer 86 and the filter disk 88 against the shoulder 83. Then, the tubing is snaked into the coupling 68, and this carries the elongate, hollow sleeve 75 through the coupling 68, through the tapered spool 70 and into the male fitting. It seats against the spacer 86 and the filter element 88, jamming the two against the shoulder 83. Thereafter, the coupling 68 is tightened, and the hollow threaded nut 56 is tightened. As these two are tightened, the grip on the tubing is completed, and the hollow, elongate sleeve 75 is jammed against the spacer and filter element. Once the threads are made fast, the components assemble to the form shown in FIG. 1.

The embodiment 50 thus makes the connection of a tubing to a male fitting. This is accomplished without regard to match or mismatch between the diameters of the tube over a range determined in large part by the practicalities of the equipment. Typically, laboratory equipment utilizes relatively small fittings, and the conduits are, themselves, in the appoximate same range. A typical range is as small as one-sixteenth inch up to about one-half inch. It is generally not necessary to have larger tubing and larger fittings. The adaptor assembly 50 thus completes this connection and accomplishes it with the installation of a filter. The filter can be selectively removed and serviced.

Attention is next directed to FIG. 3 of the drawings, where an embodiment 150 is identified. The embodiment 150 is similar in construction insofar as the adaptor assembly is concerned. Instead of a filter, the embodiment 150 incorporates a check valve. The elongate, hollow tubing is modified to include a shoulder 151 which serves as a valve seat. The shoulder 151 is a circular chamfer about the passage at the end of the passage. The passage, itself, is countersunk to define a standoff wall 152 which defines a cavity which receives a valve element 160. The valve element 160 is a round sphere which seats against the chamfered surface 151. It is moved to the illustrated position of FIG. 3 by flow in the reverse direction. This is the direction in which the flow is blocked. The check valve further incorporates a disk 161 inserted coaxially at the end of the elongate, hollow sleeve. The disk is round and relatively thick. It matches the external diameter of the hollow sleeve and bottoms against the shoulder 83 in the male fitting. It incorporates a number of holes which are drilled at 162. In the aggregate, the holes are sufficiently large that flow through the check valve is not impeded. The total cross-sectional area of the holes 162 equals or matches the cross-sectional area through the elongate, hollow sleeve. The shoulder 83 in FIG. 3 is modified at 164 so that the back side of the disk 161 is cleared, permitting flow through all of the holes drilled in it.

The check valve embodiment is assembled in the manner illustrated in FIG. 3. The sphere 160 is captured within the surrounding wall 152 about it. It cannot escape because it is blocked by the disk 161. When flow moves from the extreme right towards the left, the ball is forced to the left, and this clears the adaptor assembly for flow. Flow in the opposite direction forces the ball in advance of the flow to the valve seat 151 where the ball plugs the passage and stops flow.

The foregoing is directed to the adaptor assembly suitable for use with a male fitting. This works quite well. However, the present disclosure includes the female connector adaptor assembly shown in FIGS. 4, 5 and 6, and two embodiments are there included. The two embodiments are, again, a filter and check valve as will be described.

Attention is next directed to FIG. 4 of the drawings, where the embodiment 10 is shown in sectional view. Briefly, an adaptor assembly is illustrated cooperative with a female fitting. Again, the same reference numerals as were utilized in the referenced disclosure will be used to describe certain common parts. To this end, the numeral 12 identifies a female fitting. It is a part of a body to enable connection to be made. The precise nature of the body is not material other than to note that the female fitting is formed in it. Moreover, the female fitting is internally threaded to define a tapped opening at the end of a passage 15 to thereby enable connection to a tubing 14. The tubing 14 and the passage 15 may have a match or a mismatch in size. The adaptor of the present invention finds its best use and application in connecting mismatched conduits such as the tubing 14 which is to be connected with the passage 15 through the use of the female fitting and the adaptor assembly. The fitting 12 is thus formed in a body and has a size subject to variation. Routinely, it is constructed with an internally threaded opening of somewhat larger diameter at the end of the passage 15. Typically, it is formed with a metal body which is a part of or an accessory to a laboratory test instrument. The passage 15 might range from about one-sixteenth inch up to about one-half inch or so. Typically, sizes do not exceed this range because there is usually no need for larger passages in laboratory test equipment.

The numeral 16 refers to a hollow, threaded nut which is axially hollow and incorporates an internal passage 17 which fits about the tubing 14 somewhat loosely. It has a head at 18 which is formed with wrench flats to enable it to be easily threaded or unthreaded. Moreover, the threaded nut 16 is provided with a set of externally located threads 19 extending along the length of the body, and the nut terminates at a generally transverse face 20. The face 20 is at the end opposite from the head and is incorporated to abut the end of a tapered spool 22. The spool 22 is axially hollow and incorporates a passage 23 sized to enable it to fit around the tubing 14. The passage 23 is somewhat loose in fit, a friction fit being unnecessary. The hollow spool 22 has an external tapered face 24 which is used to nest into and against another component to be described. The tapered spool 22 is, in use, radially loaded and grips the tubing 14 when it is assembled with the other components.

The numeral 25 identifies an elongate, hollow, tubular member including an axial passage at 26. The passage 26 extends from one to the other and is smaller than the O.D. of the tubing 14. The tubing 14 is inserted into the hollow, tubular member 25 until it is arrested by a shoulder 27. The shoulder 27 limits penetration. The end where the tubing is inserted is counterbored to define a slightly larger radius adjacent to the shoulder 27, and the counterbore is flared at 29. The flared surface is a tapered, internal surface coacting with the tapered external surface 24 of the tapered spool. These two surfaces enable the components to nest together as will be described.

The elongate, hollow sleeve 25 serves as an extension for the tubing 14. This will be understood in detailed description of assembly. The elongate, hollow sleeve 25 passes fully through a coupling 28 which coacts with a larger, tapered spool 30. The spool 30 has an end face 31 which abuts an end face 32 on the coupling. It also has a tapered external face 33 and an axial passage 34. The passage 34 is sufficiently large to receive the sleeve 25 through it. The sleeve, therefore, passes through both the coupling and the tapered spool. This can be observed in contrasting FIG. 4, where the components are shown assembled.

The fitting 12 is internally threaded at 37 and has a tapered internal surface 38 which narrows the diameter of the passage from the larger portion where the threads 37 are found to the smaller passage 15. There is an end located shoulder 39 which defines the end of the contersunk portion of the fitting located at the terminus of the passage 15. The threads 37 engage matching threads 40 formed on the exterior of the coupling 28. An enlargement functioning somewhat as a large, hollow head with wrench flats is found at 41. The wrench flats enable the coupling 28 to be threaded and tightened into the female fitting. The coupling 28 is threaded to the fitting 12 with the tapered spool 30 between the two. The tapered spool 30 limits penetration. The elongate sleeve enters the female fitting until it abuts against the shoulder 39 where entrance is thereby limited.

The coupling 28 is internally threaded at 44 and is provided with a set of threads on the interior to engage the threads 19 on the hollow nut 16. The coupling thus adopts a smaller size to a larger size, and, to this end, the coupling 28 is formed with threaded diameters and wall thicknesses to accommodate the conversion in size. This enables accommodation of mismatches in tubing sizes.

The present invention in particular includes a perforated, cylindrical disk 45 which is very similar to the perforated disk 161 shown in FIG. 3 and which has a plurality of holes in it, the total cross-sectional area providing a flow path without restriction. The chek valve apparatus also incorporates a sphere 46 which serves as a valve element. The sphere is received within and captured by a skirt 47 which is formed by counterboring the elongate, hollow tube 25. The counterbore defines an internal cavity at the end to receive the sphere with some room for movement. The end of the passage 26 is defined by the chamfered surface 48 which serves as a valve seat. The valve seat receives the sphere 46 against it to serve as a check valve blocking flow from left to right as viewed in FIGS. 4 and 5.

Assembly of the equipment should be noted. Briefly, the tubing 14 is slipped completely through two components and into a third. It is shown passing fully through the hollow nut 16 and the tapered spool 22. It enters the elongate sleeve 25 and abuts the shoulder 27 on the interior. This is then inserted fully through the coupling 28 and the spool 30. The hollow sleeve 25 is inserted into the female fitting. Before it is inserted, however, the disk 45 and the ball element 46 are positioned at the end of the sleeve, aligned with the passage in the female fitting and bottomed against the shoulder 39. At this juncture, the large, tapered spool 30 is pushed into the female fitting, and the coupling 28 is tightened a few turns to seat in position the tapered spool. The threaded nut is also tightened to at least finger tightness. The coupling 28 is tightened fully, and the hollow, threaded nut 16 is also tightened. This connects the tubing 14 with the fitting and, moreover, installs the check valve.

The apparatus of the present invention is then made fast by snugging the coupling 28 and the hollow nut 16. It will be observed that the large, tapered spool 30 has an angle which is slightly different from the seat which receives it. It is helpful so that a snug fit is taken. Moreover, this enhances the radial grip achieved to hold the components together, even though an axial pull is placed on the tubing 14. The tubing 14 is held against slippage and is gripped around the exterior by the radial loading formed against it on jamming the small, tapered spool 22 into the end tapered surface 29. This creates a radial force which grips the tubing 14 and holds the tubing in position. Thus, the tubing 14 is shown loosely received in the hollow nut 16. It has less clearance in the hollow, tapered spool 22, and that spool shrinks on the interior to grip the tubing when the threads are made fast.

The embodiment shown in FIGS. 4 and 5 is a check valve adaptor assembly cooperative with a female fitting. FIG. 6 depicts the modifications necessary to disclose and describe an adaptor assembly for use with a female fitting which incorporates a filter. It can be used with the countersunk end bore construction shown in FIG. 5 for the elongate, hollow sleeve. Alternatively, the tip of the sleeve can be modified. In any event, the numeral 180 identifies a disk of fibrous material which functions as a filter. Since significant axial loading is placed on it, it is protected either with a recessed cavity of the sort shown in FIG. 5, where the disk 180 is positioned, or, in the alternative, the disk is constructed with a surrounding external ring of the sort shown in FIG. 2. In either case, a filter construction is provided. The term "flow control means" thus includes the various embodiments of filter and check valve disclosed herein.

An important factor to note with the alternate embodiments of the present invention (both male and female connectors with either a check valve or filter construction) is that they can be used with matched or mismatched tubular members. In particular, there is an advantage in accommodating mismatched tubular members, the mismatch typically occurring on the use of tubular members in the range of about one-sixteenth to about one-half inch. These sizes are typical of laboratory test instruments.

While the foregoing is directed to the preferred embodiment, the scope of the present invention is determined by the claims which follow.

I claim:

1. An adaptor for connecting a tubing to a fitting to accommodate interconnection therebetween which comprises:
   (a) a hollow nut adapted to be positioned about a tubing;
   (b) an elongate, hollow, tubular sleeve having an internal passage and first shoulder therein facing the end of the tubing;
   (c) a first tapered spool adapted to be forced into the end of said sleeve by said nut and surrounding said tubing to wedge against the tubing and thereby grip around the tubing;
   (d) an elongate coupling having:
      (1) an axial passage therethrough;
      (2) a first set of threads at one end of said passage for engaging said hollow nut;
      (3) a second set of threads for connection to a male or female fitting;
      (4) a second shoulder facing away from the end at which said hollow nut is threaded to said coupling;
      (5) a radial thickness in said coupling defined between the radii of said first and second sets of threads which is at least in part related to the relative diameters of the tubing and the fitting;
      (6) means defining a receptacle for receiving that portion of said tubular sleeve that is remote from said tubing and defining a tapered internal seat surface surrounding said tubular sleeve, said means also defining an internal passage and a third shoulder therein facing the ends of said tubing and tubular sleeve;
   (e) a second tapered spool adapted to be abutted against said second shoulder and inserted into said tapered internal seat surface in said fitting surrounding said hollow sleeve and wedging thereagainst to grip said sleeve in axial communication with a passage through the fitting;
   (f) force transmission means disposed within said receptacle and being in force transmitting engagement with said third shoulder and the end of said tubular sleeve; and
   (g) flow control means located within said receptacle and being serially in communication with the passage in the fitting and the tubing and clamped between said hollow nut and the fitting on threaded assembly with said elongate coupling.

2. The apparatus of claim 1 wherein said force transmission means is of annular configuration and defines a filter chamber therein and said flow control means comprises a filter being located within said filter chamber and positioned to filter material passing through said passage.

3. The apparatus of claim 1 wherein said flow control means comprises a check valve having:
   (a) a chamfered shoulder along said passage in said sleeve;
   (b) a valve element comprising a spherical valve element sized to plug said passage upon seating against said chamfered shoulder;
   (c) a surrounding, hollow, tubular member sufficiently large to receive said valve element therein and to permit movement thereof toward and away from said chamfered shoulder; and
   (d) said force transmission means is valve retainer means adapted to be positioned transverse to the passage and immediately adjacent to said valve element to constrain movement of the valve element away from said chamfered seat, said valve retainer means having an aggregate cross-sectional flow area exceeding a specified flow area.

4. The apparatus of claim 3 wherein said flow control means further comprises an end located, counterbore, surrounding peripheral lip defined on the sleeve having an internal counterbored volume to receive said flow control means therein.

5. The apparatus of claim 3 wherein said flow control means comprises an internally chamfered shoulder on the sleeve at the passage in the sleeve and a movable valve element in the passage responsive to direction of flow in the passage to move against said shoulder to close the passage.

* * * * *